United States Patent [19]

Hakamatsuka et al.

[11] Patent Number: 4,799,887
[45] Date of Patent: Jan. 24, 1989

[54] GLASS CERAMIC DENTAL CROWN AND METHOD OF MANUFACTURING THE SAME

[75] Inventors: Yasuharu Hakamatsuka; Kazuhiro Watanabe, both of Tokyo, Japan

[73] Assignee: Olympus Optical Co., Ltd., Tokyo, Japan

[21] Appl. No.: 879,355

[22] Filed: Jun. 27, 1986

[30] Foreign Application Priority Data

Jul. 5, 1985 [JP] Japan ................................ 60-147932

[51] Int. Cl.⁴ .................... A61C 13/08; C03C 10/16
[52] U.S. Cl. ................ 433/212.1; 433/201.1; 501/3; 501/7; 501/57
[58] Field of Search ............ 433/201.1, 212.1, 218, 433/222.1; 501/3, 7, 57

[56] References Cited

U.S. PATENT DOCUMENTS

| | | | |
|---|---|---|---|
| 2,933,458 | 4/1960 | King et al. | 501/57 X |
| 4,604,059 | 8/1986 | Klaus et al. | 433/218 X |
| 4,652,312 | 3/1987 | Grossman et al. | 501/3 X |

FOREIGN PATENT DOCUMENTS 37-14912  9/1962  Japan .
51-73019  6/1976  Japan .

*Primary Examiner*—Richard J. Apley
*Assistant Examiner*—Alan W. Cannon
*Attorney, Agent, or Firm*—Frishauf, Holtz, Goodman & Woodward

[57] ABSTRACT

A dental crown is prepared from a dental crown material including 7 to 11% by weight of $Li_2CO_3$, 18 to 28% by weight of MgO, 9 to 15% by weight of $Al_2O_3$, 38 to 48% by weight of $SiO_2$ and 10 to 15% by weight of $Na_2SiF_6$. The dental crown material is melted and the molten material is molded in a lost wax mold. The molded material is crystallized to form the dental crown.

7 Claims, 2 Drawing Sheets

GLASS CERAMIC DENTAL CROWN AND METHOD OF MANUFACTURING THE SAME

BACKGROUND OF THE INVENTION (1) Field of the Invention

This invention relates to a glass ceramic dental crown and a method for manufacturing the same.

(2) Description of the Prior Art

The lost wax process has hitherto been known as the technique of fabricating a dental crown. To describe briefly, the process involves applying wax on a damaged tooth to prepare a wax pattern, investing the wax pattern with a mold material or an investing material, and hardening the investing material. The wax pattern is then thermally removed to provide a mold. A dental crown material is cast in the mold to fabricate the predetermined dental crown.

Hitherto, metallic materials including alloys have been used as a dental crown material. However, the metallic materials constitute a chemical battery in the oral cavity, and dissolve out metal ions within the oral cavity, tending to harmfully affect the human body. Moreover, the metallic material has a less attractive appearance, and, what is worse, frequently imparts an unpleasant feeling to the user due to different thermal conductivity between the natural tooth and the metallic dental crown.

Recently, a new artificial dental crown has been proposed which is prepared from crystallized glass of the calcium phosphate series. The crystallized glass of the calcium phosphate series has a composition resembling that of a natural tooth as described in Japanese Patent Disclosure No. 51-73019, and is regarded as adaptable as a dental crown material. At present, clinical research work is undertaken on the proposed new dental crown material. The proposed artificial dental crown is fabricated by adding a nucleating material to relatively low melting glass of the calcium phosphate series (for example, $CaO-P_2O_5$, $CaO-Al_2O_3-P_2O_5$), melting the mixture, molding the molten mass in the lost wax mold, and thermally treating the resultant transparent glass dental crown at a temperature approximating the crystal-precipitating level, thereby crystallizing the glass.

However, the conventional dental crown material prepared from the crystallized glass of the calcium phosphate series reacts with the investing material such as cristobalite during the heat treatment for crystallization. As a result, the surface of the fabricated dental crown is roughened to adversely affect its color and transparency. Further, the glass of the calcium phosphate series constituting the conventional dental crown has one-dimensional or two-dimensional structure, namely, chain-like structure, and consequently has a lower chemical durability than the silicate glass having a three-dimensional structure. Moreover, the conventional dental crown has further drawbacks that when subjected to thermal crystallization, the conventional dental crown presents difficulties in attaining a uniform and compact crystallized structure, and the crown is reduced in mechanical strength.

SUMMARY OF THE INVENTION

It is accordingly an object of the present invention to provide a mechanically strong dental crown whose surface is not roughened, and a method of manufacturing such a crown.

According to a first aspect of the present invention, a glass ceramic dental crown is provided which is prepared from a dental crown material comprising 7 to 11% by weight of $Li_2CO_3$, 18 to 28% by weight of MgO, 9 to 15% by weight of $Al_2O_3$, 38 to 48 % by weight of $SiO_2$ and 10 to 15% by weight of $Na_2SiF_6$.

According to a second aspect of the invention, there is provided a method of manufacturing a glass ceramic dental crown, comprising the steps of:

melting the above-mentioned dental crown material according to this invention;

molding the molten mass in a crown-shaped mold fabricated by the lost wax process; and thermally crystallizing the molded mass within or out of said mold.

DETAILED DESCRIPTION OF THE PREFERRED EMBODIMENTS

As mentioned above, the glass ceramic dental crown according to this invention is prepared from a dental crown material including 7 to 11% by weight of $Li_2CO_3$, 18 to 28% by weight of MgO, 9 to 15% by weight of $Al_1O_3$, 38 to 48% by weight of $SiO_2$ and 10 to 15 % by weight of $SiF_6$. The dental crown material may further include from 1 to 7% by weight of ZnO, $CaF_2$, etc. and/or from 0.1 to 2% by weight of coloring material such as $Fe_2O_3$, CeO, MnO, NiO etc. Particularly when the dental crown material is blended with from 2 to 6% by weight of $ZrO_2$ and/or $Y_2O_3$, the resultant dental crown is elevated in resistance to water and acids.

The dental crown material according to this invention may be made suitable for anterior teeth. The dental crown composition most suitable for anterior teeth comprises 7 to 8% by weight of $Li_2CO_3$, 21 to 22% by weight of MgO, 10% by weight of $Al_2O_3$, 43.5% by weight of $Si_{O2}$, 12 to 13% by weight of $Na_2SiF_6$, 2 to 3% by weight of ZnO, 2 to 3% by weight of ZrO, 0.5% by weight of CeO, 0.01% by weight of $Fe_2O_3$ and 0.06% by weight of NiO.

The dental crown material of the invention may further be made suitable for molar teeth. The dental crown composition most suitable for molar teeth comprises 10 to 11% by weight of $Li_2CO_3$, 20 to 21% by weight of MgO, 14 to 15% by weight of $Al_2O_3$, 40 to 41% by weight of $Si_{O2}$, 10 to 11% by weight of $Na_2SiF_6$, 3 to 4% by weight of ZrO, 0.5% by weight of $TiO_2$, 0.1% by weight of $Y_2O_3$ and 0.5% by weight of CeO.

Figure 1A:
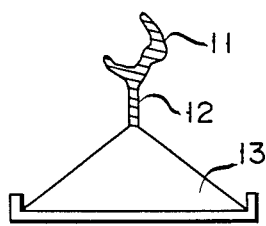
FIGS. 1A to 1D schematically show the sequential steps of manufacturing a dental crown according to this invention.
Figure 1B:
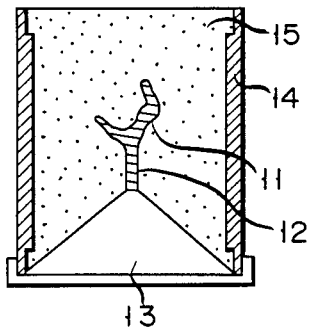
Figure 1C:
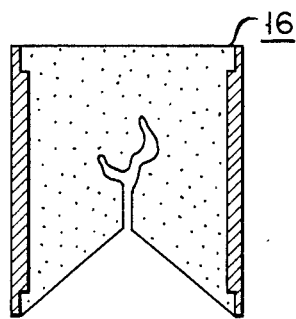
Figure 1D:
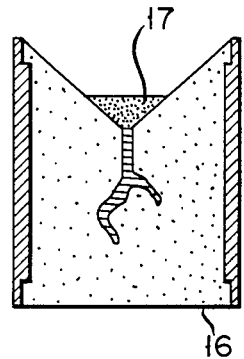

The known lost wax process is adapted for the preparation of a glass ceramic dental crown from the dental crown material according to this invention. First as shown in FIG. 1A, wax is applied to a damaged tooth to fabricate a wax pattern 11. Wax sprue line 12 is attached to wax pattern 11. The whole assembly is allowed to stand at the apical point of crucible former or conical sprue base 13 by being fixed at the bottom end of sprue line 12. Sprue base 13 is then surrounded by casting ring 14, as shown in FIG. 1B. Investing material 15 of cristobalite series is filled in casting ring 14 and investing material 15 is hardened. Later as shown in FIG. 1C, wax pattern 11 and sprue line 12 are thermally removed, thereby providing lost wax mold 16. Later as illustrated in FIG. 1D, dental crown material 17 according to this invention is molten at a temperature ranging between 1350° and 1400° C. The molten mass is cast into lost wax mold 16. After hardened in lost was mold 16, the dental crown material is again thermally treated for crystallization at a temperature ranging between 720° and 750° C. in the mold 16 or a separate furnace. The time of thermal treatment generally ranges between 2 hours and 2.5 hours. At the time of the heat treatment, mica crystal phase and spodumene crystal phase settle out in the glass ceramics, thus providing a uniform and dense crystalline structure. The more voluminous the spodumene crystal phase which has settled out, the greater the mechanical strength of the resultant dental crown. It is preferred that the spodumene crystal phase be contained in the dental crown at the rate ranging between 5% by weight and 10% by weight. Further, the dental crown is more improved in machinability and has a more dense structure, as it contains a larger amount of mica crystal phase which has settled out. It is preferred that the mica crystal phase be contained in the dental crown at the rate ranging between 10% by weight and 20% by weight.

After the thermal treatment is finished, the molded mass is taken out of the mold, and that portion of the molded mass which corresponds to the sprue line 12 is cut off. Thus is formed the dental crown according to this invention.

The dental crown material used in this invention does not react with cristobalite investing material, thus offering the advantages that the heat treatment of the glass crystallization is conveniently performed in the lost wax mold and the resultant dental crown has a smooth surface.

The present invention will become more apparent with reference to the examples which follow.

EXAMPLE 1

Three samples having compositions shown in Table 1 below were respectively molten at a temperature of 1400° C. for one hour, providing transparent glass.

TABLE 1

| Sample | $Li_2CO_3$ | MgO | $Al_2O_3$ | $SiO_2$ | $Na_2SiF_6$ |
|---|---|---|---|---|---|
| No. 1 | 8.6 | 28.0 | 11.8 | 37.1 | 14.5 |
| No. 2 | 9.4 | 24.2 | 13.4 | 39.5 | 12.6 |
| No. 3 | 10.8 | 21.2 | 14.9 | 42.1 | 11.0 |

Note: The numbers given above represent % by weight.

Figure 2:
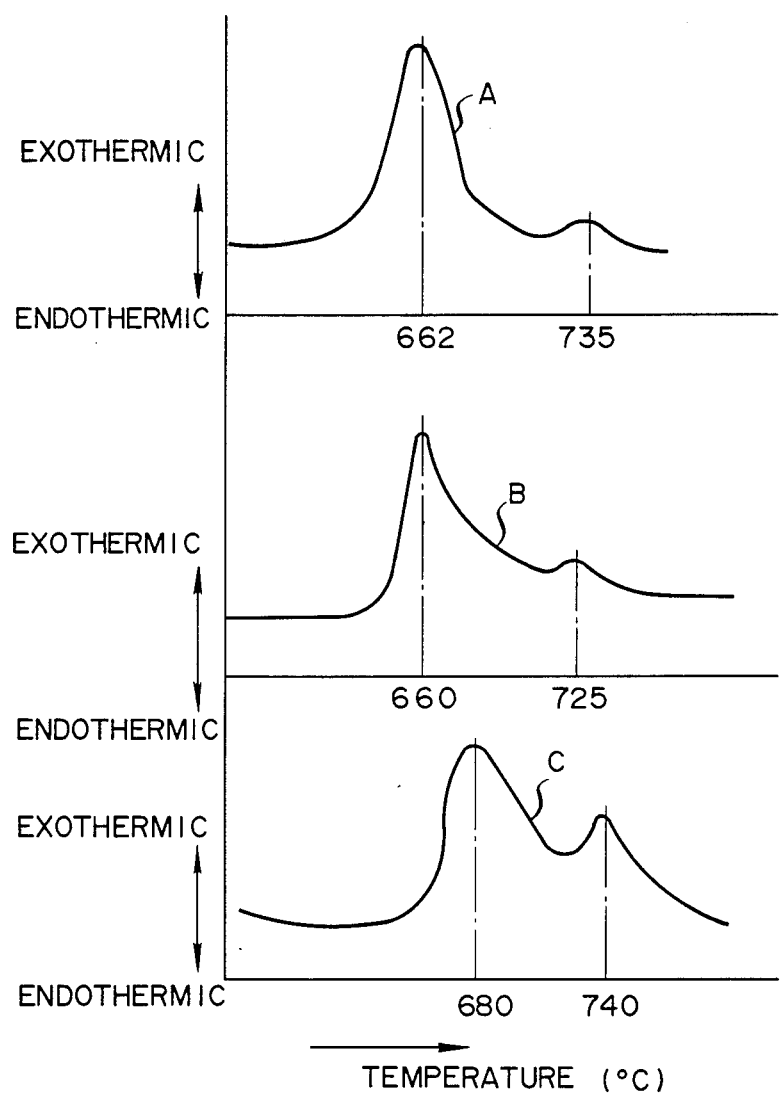
FIG. 2 shows graphs indicating the results of the differential thermal analysis of the dental crown material according to this invention.

Heating peak temperature was determined by differential thermal analysis in order to define a temperature required for the thermal crystallization of the respective samples. Curve A in FIG. 2 denotes the spectrum of Sample No. 1 having the largest content of MgO and $Na_2SiF_6$. Curve B represents the spectrum of sample No. 2 having a medium content of MgO and $Na_2SiF_6$. Curve C shows the spectrum of sample No. 3 containing least MgO and $Na_2SiF_6$.

Molten samples Nos. 1-3 were cast into a mold fabricated by the lost wax process, and molded into shape, using a centrifugal casting machine. After the molding, the glass dental crown embedded in the mold was heat treated in tact for crystallization. The crystallization treatment involved maintaining the glass dental crown at 750° C. for 2 hours, raising the temperature up to 950° C. and then allowing the dental crown to cool to room temperature. At this time, substantially no reaction took place between the embedded glass dental crown and the cristobalite investing material, providing a dental crown having a smooth surface.

Table 2 gives the comparison of the various properties of the dental crowns of this invention, a porcelain dental crown and a dental crown prepared from $CaO$-$P_2O_5$ crystallized glass.

TABLE 2

| Physical properties | Samples of the present invention | | | Porcelain dental crown | Dental crown prepared from $CaO$—$P_2O_5$ crystallized glass |
|---|---|---|---|---|---|
| | No. 1 | No. 2 | No. 3 | | |
| Compression strenghth | Good | Good | Good | Good | Good |
| Indirect tensile strength | | | Slightly good | Low | Slightly good |
| Bending strength | | | Good | Slightly good | Good |
| Knoop hardness | Good | Good | Slightly good | Low | Good |
| Machinability | Good | Good | Slightly good | Low | Slightly |
| Biocompatibility | Good | Good | Good | Slightly good | Good |
| Chemical durability* | Good | Good | Good | Good | Slightly good |
| Color | Same as a natural tooth | Same as a natural tooth | Same as a natural tooth | Same as a natural tooth | Same as a natural tooth |

*Chemical durability: Sample glass powder pulverized to 420–590 μm was put in a platinum vessel and the vessel was immersed in a test liquid contained in a round-bottomed flask. The flask was heated ina boiling water bath for 60 minutes. The weight decrease of the glass powder was measured. The test liquid used was distilled water (pH: 6.5–7.5) in the case of water resistance test, and was 0.01 N nitric acid in the case of acid resistance test.

resistance test, and was 0.01N nitric acid in the case of acid resistance test.

Table 2 above shows that the samples of the present invention have properties the same as or higher than those of the porcelain dental crown and the dental crown prepared from $CaO$-$P_2O_5$ crystallized glass in respect of compression strength, indirect tensile strength, bending strength, Knoop hardness, machinability, biocompatibility, chemical durability and color. Referring to mechanical strength, it has been found that the sample of this invention in which the spodumene crystal phase has noticeably settled out indicates a correspondingly great mechanical strength. It has also been discovered that the larger content of mica crystal phase ensures the better machinability and greater compactness of the resultant dental crown.

The dental crown of this invention is possessed of not only affinity to living body, but also, when heat treated, presents mica crystal phase and spodumene crystal phase, and consequently indicates great machinability and mechanical strength after molded. Moreover, this present invention can manufacture a glass ceramic dental crown having a proper mechanical strength suitable for the anterior tooth or molar tooth by varying the relative proportions of the mica crystal phase and spodumene crystal phase.

EXAMPLE 2

The glass of sample No. 1 of Example 1 was heated at 750° C. for 2 hours and later heated up to 900° C., and later allowed to cool, thus providing crystallized glass. Further, the glass of sample No. 1 of the present invention was mixed with 4 % by weight of zirconia ($Zro_2O$) and 0.1% by weight of yttria ($Y_2O_3$), thus providing glass sample No. 4. The sample No. 4 was treated in the same manner as mentioned above to provide crystallized glass. These two crystallized glass were pulverized into particles whose diameter ranged between 500 and 900 microns. 5 grams of each powder were taken into separate flasks, each of which contained 100 cc of a 0.01 normal solution of nitric acid or ion exchange water having pH of about 7. The flasks were dipped for 1 hour in a water bath boiling at 100° C. Measurement was made of a decrease in the weight of the respective crystallized glass powders, the results being set forth in Table 3 below.

TABLE 3

| Sample | Decrease in weight (% by wt.) | |
| --- | --- | --- |
|  | Ion exchange water | Nitric acid |
| No. 1 | 0.09 | 0.37 |
| No. 4 | 0.04 | 0.19 |

Table 3 above shows that the crystallized glass to which zirconia and yttria were added was improved in the resistance to water and acid.

As described above, this invention provides a dental crown which has a satisfactory biocompatibility, smooth surface and great mechanical strength, by a relatively simple method.

What is claimed is:

1. A glass ceramic dental crown prepared from a dental crown material comprising 7 to 11% by weight of $Li_2CO_3$, 18 to 28% by weight of $SiO_2$ and 10 to 15% by weight of $Na_2SiF_6$ and having 5-10% by weight of a spodumene crystal phase and 10-20% by weight of a mica crystal phase.

2. The dental crown according to claim 1, wherein said dental crown material further contains at least one member selected from the group consisting of ZnO and $CaF_2$.

3. The dental crown according to claim 1, wherein said dental crown material further contains at least one coloring agent selected from the group consisting of $Fe_2O_3$, CeO and MnO.

4. The dental crown according to claim 1, wherein said dental crown material further contains at least one member selected from the group consisting of $ZrO_2$ $Y_2O_3$.

5. The dental crown according to claim 1, wherein said dental crown material includes 7 to 8% by weight of $Li_2CO_3$, 21 to 22% by weight of MgO, 10% by weight of $Al_2O_3$, 43.5% by weight of $SiO_2$, 12 to 13% by weight of $Na_2SiF_6$, $2SiF6$, 2 to 3% by weight of ZnO, 2 to 3% by weight of ZrO, 0.5% by weight of CeO, 0.01% by weight of $Fe_2O_3$, and 0.06% by weight of NiO.

6. The dental crown according to claim 1, wherein said dental crown material includes 10 to 11% by weight of $Li_2CO_3$, 20 to 21% by weight of MgO, 14 to 15% by weight of $Al_2O_3$, 40 to 41% by weight of $SiO_2$, 10 to 11% by weight of $Na_2SiF_6$, 3 to 4% by weight of ZrO, 0.5% by weight of $TiO_2$, 0.1% by weight of $Y_2O_3$ and 0.5% by weight of CeO.

7. The dental crown according to claim 1 wherein said dental crown material is crystallized.

* * * * *

UNITED STATES PATENT AND TRADEMARK OFFICE
CERTIFICATE OF CORRECTION

PATENT NO.  : 4,799,887
DATED       : January 24, 1989
INVENTOR(S) : HAKAMATSUKA et al It is certified that error appears in the above-identified patent and that said Letters Patent is hereby corrected as shown below:

Column 5, line 32 (Claim 1): after "28%" insert
--by weight of MgO, 9 to 15% by weight
of $Al_2O_3$, 38 to 48%--.

Signed and Sealed this

Eighth Day of November, 1994

Attest:

BRUCE LEHMAN

Attesting Officer

Commissioner of Patents and Trademarks